United States Patent
Bergelson et al.

(10) Patent No.: US 7,848,813 B2
(45) Date of Patent: **\*Dec. 7, 2010**

(54) SYSTEM AND METHOD FOR REAL-TIME REMOTE MONITORING OF IMPLANTABLE MEDICAL DEVICES

(75) Inventors: Michael Bergelson, Bronx, MN (US); Narcis M. Naydenov, Wayne, NJ (US)

(73) Assignee: Medtronic, Inc., Minneapolis, MN (US)

( \* ) Notice: Subject to any disclaimer, the term of this patent is extended or adjusted under 35 U.S.C. 154(b) by 999 days.

This patent is subject to a terminal disclaimer.

(21) Appl. No.: 11/554,789

(22) Filed: Oct. 31, 2006

(65) Prior Publication Data

US 2007/0106346 A1 May 10, 2007

Related U.S. Application Data

(63) Continuation of application No. 10/672,228, filed on Sep. 26, 2003, now Pat. No. 7,218,967.

(51) Int. Cl.
*A61N 1/00* (2006.01)

(52) U.S. Cl. .................................................. 607/32
(58) Field of Classification Search ............. 607/9–32, 607/59, 60
See application file for complete search history.

(56) References Cited

U.S. PATENT DOCUMENTS

| | | | | |
|---|---|---|---|---|
| 4,281,664 | A | \* | 8/1981 | Duggan ....................... 600/508 |
| 5,300,093 | A | \* | 4/1994 | Koestner et al. .............. 607/32 |
| 2001/0012955 | A1 | \* | 8/2001 | Goedeke et al. .............. 607/27 |

\* cited by examiner

*Primary Examiner*—Scott M Getzow

(57) ABSTRACT

A patient monitor is configured to interrogate an implantable medical device (IMD) and receive data from the IMD in response to the interrogation. The data received from the IMD includes electrogram (EGM) data, which the patient monitor frequency modulates for transmission, in real-time, onto a conventional telephone line. The frequency modulated EGM data that is transmitted from the patient monitor may in turn be displayed, in real-time, at a remote monitoring station in response to commands provided by a remote (DTMF) signal from a receiving station.

13 Claims, 8 Drawing Sheets

SYSTEM AND METHOD FOR REAL-TIME REMOTE MONITORING OF IMPLANTABLE MEDICAL DEVICES

CROSS REFERENCE TO RELATED APPLICATION

This application is a continuation application of U.S. Ser. No. 10/672,228 filed Sep. 26, 2003 now U.S. Pat. No. 7,218, 967 entitled "System and Method for Real-Time Remote Monitoring of Implantable Medical Devices".

FIELD OF THE INVENTION

The present invention relates to implantable medical devices (IMDs) and, more particularly, to a system and method for real-time remote monitoring of an IMD.

BACKGROUND OF THE INVENTION

Various types of devices have been developed for implantation into the human body to provide various types of health-related therapies and/or monitoring. Examples of such devices, generally known as implantable medical devices (IMDs), include cardiac pacemakers, cardioverter/defibrillators, cardiomyostimulators, cardiac event monitors, various physiological stimulators including nerve, muscle, and deep brain stimulators, various types of physiological monitors, and drug delivery systems, just to name a few. Some IMDs include varying amounts of electronic memory that may be used to store not only device operating and control software, but to store various types of patient- and device-related data. In addition, some of these same IMDs may include signal processing and telemetry circuitry, which allows some or all of the data stored in the memory to be transmitted to a remote computer network or other communication node, and/or the device to receive and store data transmitted to it remotely from a computer network or other communication node.

In many cases, after an IMD has been implanted in a patient, the patient may need to have periodic follow-up visits with a doctor or other type of practitioner. Alternatively, or in addition to periodic follow-up visits, patients with IMDs may need to periodically initiate a communication with a doctor or other type of practitioner at a medical facility or clinic, or periodically initiate a remote communication, such as described above, between the IMD and a remote network or other communications node. These periodic visits and/or communications, allow doctors or other practitioners to check the IMD and patient to determine, for example, whether or not the IMD is operating as programmed or perhaps should be programmed differently. These periodic visits and/or communications also allow, among other things, doctors or other practitioners to analyze some or all of the data stored in and/or transmitted from the IMD. These data can provide the doctor or other practitioner with various types of physiological data about the patient, and may also be used to determine whether or not the IMD is functioning properly.

In many instances, the above-described remote monitoring occurs over the telephone infrastructure. In particular, a patient monitor device, which is located in the patient's home, may be connected to a telephone jack in the patient's home, and may include one or more monitor electrodes, and a monitor wand. The monitor electrodes may be used to sense certain physiological parameters associated with the patient. The monitor wand may include a radio frequency (RF) antenna to receive the above-mentioned patient- and device-related data that may be transmitted by the IMD. Periodically, a remote station operator will call the patient and instructs the patient to transfer certain data from the IMD to the patient monitor. The operator may additionally instruct the patient to attach one or more of the monitor electrodes. For example, if the IMD is an implantable pulse generator (IPG), the operator may instruct a patient to place surface electrocardiogram (ECG) electrodes and the monitor wand on or near the chest cavity, where the IPG is located. When the electrodes and wand are properly positioned, the patient monitor receives various types of data from the patient and IPG, via the electrodes and the monitor wand, respectively. Such data may include surface ECG data, electrogram (EGM) data, physiological-related data, and various other device-specific data.

As was just noted, the data that is collected from the patient and IPG is transmitted to a remote monitoring station via a telephone line. Thus, only some of the data that is collected by the patient monitor may be transmitted in real-time to the remote monitoring station, while other data is first stored in the patient monitor, and is then transmitted from the patient monitor to a remote monitoring station. For example, surface ECG data may presently be transmitted over the telephone line in real-time; however, much of the data obtained from the implant real-time interrogation, namely device EGM data may not be transmitted in real-time.

The collection and transmission of such data in real-time would allow a remote operator to view the results of IMD interrogation while the patient and IMD are being monitored. This would allow the remote operator to remotely control the patient monitor in real-time while the patient and IMD are being monitored. This would additionally allow the remote operator to instruct the patient, in real-time, on procedural matters, such as proper placement of the wand and/or proper placement of the surface electrodes.

Hence, there is a need for a system and method that provides for real-time collection and transmission of implant-related data, and that provides for real-time transmission to, and display at, a remote monitoring site of the implant-related data simultaneously with surface ECG data. The present invention addresses one or more of these needs. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

In one exemplary embodiment, a method of transmitting a plurality of electrogram (EGM) signals associated with an implantable medical device (IMD) via a telephone line includes receiving at least first and second EGM signals from the IMD. The first and second EGM signals are frequency modulated, and the frequency modulated first and second EGM signals are transmitted onto the telephone line.

In another exemplary embodiment, an implant monitor for monitoring an implantable medical device (IMD) includes an RF receiver, a frequency modulation circuit, and an amplifier circuit. The RF receiver is adapted to receive an RF signal modulated with at least first and second electrogram (EGM) data and transmitted from the IMD. The RF receiver is configured to demodulate the first and second EGM data from the received RF signal. The frequency modulation circuit is coupled to receive the demodulated first and second EGM data and a substantially fixed-frequency signal, and is configured to frequency modulate the fixed-frequency signal based on the demodulated first and second EGM data and supply first and second frequency modulated EGM data signals. The amplifier circuit is coupled to receive the first and second frequency modulated EGM data signals, and is configured to supply a composite frequency modulated signal.

In yet another exemplary embodiment, a method of frequency modulating digital data transmitted from an implantable medical device (IMD) includes periodically sampling the transmitted digital data to supply a sampled digital data value, and initializing a counter to the sampled digital data value. The counter is incremented at a fixed frequency until the counter reaches a predetermined value, at which point a pulse is generated.

BRIEF DESCRIPTION OF THE DRAWINGS

The present invention will hereinafter be described in conjunction with the following drawing figures, wherein like numerals denote like elements, and wherein.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the drawings. In this regard, before proceeding with the detailed description, it is to be appreciated that the described embodiment is not limited to use in conjunction with a specific type of implantable medical device (IMD). Thus, although the present embodiment is, for convenience of explanation, depicted and described as being implemented in an implantable pulse generator (IPG), it will be appreciated that it can be implemented in various other IMDs.

Figure 1:
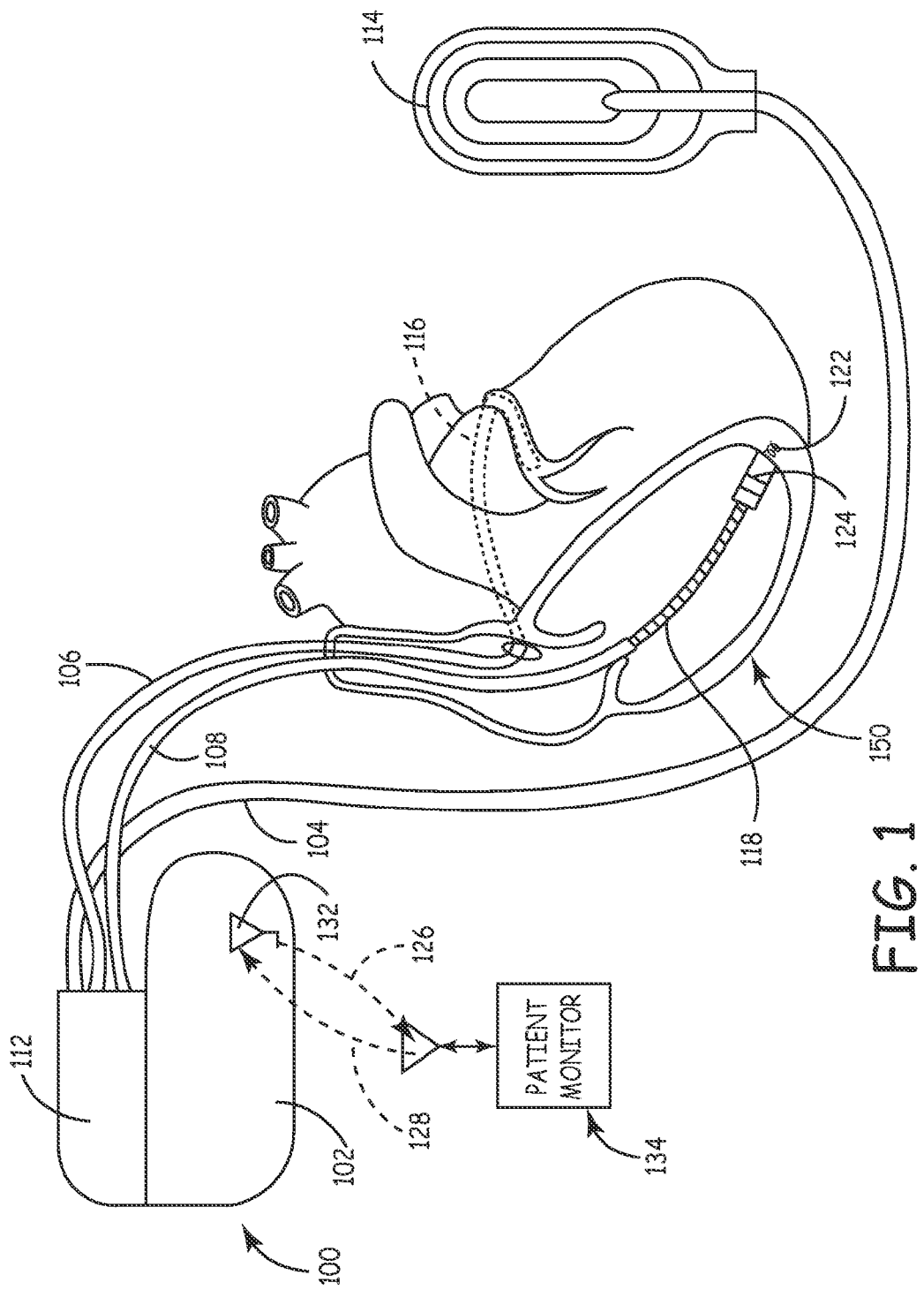
FIG. 1 is a perspective view of an implantable pulse generator coupled to a heart and which is exemplary of one type of implantable medical device (IMD) that may incorporate an embodiment of the present invention.

Turning now to the description and with reference first to FIG. 1, a simplified representation of an IPG 100 and its connection to a patient heart 150 is shown. The IPG 100 includes a housing 102 and a plurality of leads, including a first lead 104, a second lead 106, and a third lead 108. The housing 102 is preferably formed of a suitable, internal body compatible material that has been approved for medical use, such as, for example, titanium. The housing 102 is preferably hermetically sealed, so that it is substantially impervious to body fluids, and is suitably physiologically shaped to substantially avoid any sharp edges, so that tissue damage during and after implantation can be substantially avoided. The housing 102 includes a connector header 112, which includes separate connector ports and feedthroughs (neither are shown), at least one for each lead 104-108. The connector ports each electrically couple one of the leads 104-108 to one of the feedthroughs, which in turn electrically couples the connector port to the associated circuitry housed within the housing 102. A detailed description of at least a portion of this circuitry is provided further below.

The first, second, and third leads 104-108, each of which include a plurality of conductors, extend from the housing 102 and include first, second, and third electrodes, 114, 116, and 118, respectively, that can be used for pacing, sensing, and/or pulse generation. When implanted in a patient, the first lead 104 extends subcutaneously from the housing 102, and the first electrode 114 is mounted in the patient's chest cavity proximate the heart 150. The second lead 106 extends subcutaneously from the housing 102 and into the patient heart 150. Specifically, the second lead 106 extends transvenously into the heart 150 and, more particularly, into the coronary sinus and down any cardiac vein accessible from the coronary sinus. The second electrode 116 is disposed in the heart 150 such that it extends from a point within the opening of the coronary sinus to the vicinity of the left ventricle. Similarly, the third lead 108 extends transvenously into the heart 150 and, more particularly, into the right ventricular chamber, in which the third electrode 118 is disposed. As is generally known, cardioversion-defibrillation shocks may be applied, when needed, between selected pairs of the first 114, second 116, and third 118 electrodes, according to any one of various defibrillation regimens. It is additionally noted that, in the depicted embodiment, the third lead 108 is also terminated with a pair of ventricular pace/sense electrode 122 and 124. These ventricular pace/sense electrodes are used to provide cardiac pacing pulses, and may be additionally employed to provide near field and/or far field EGM ventricular sensing capabilities.

Figure 2:
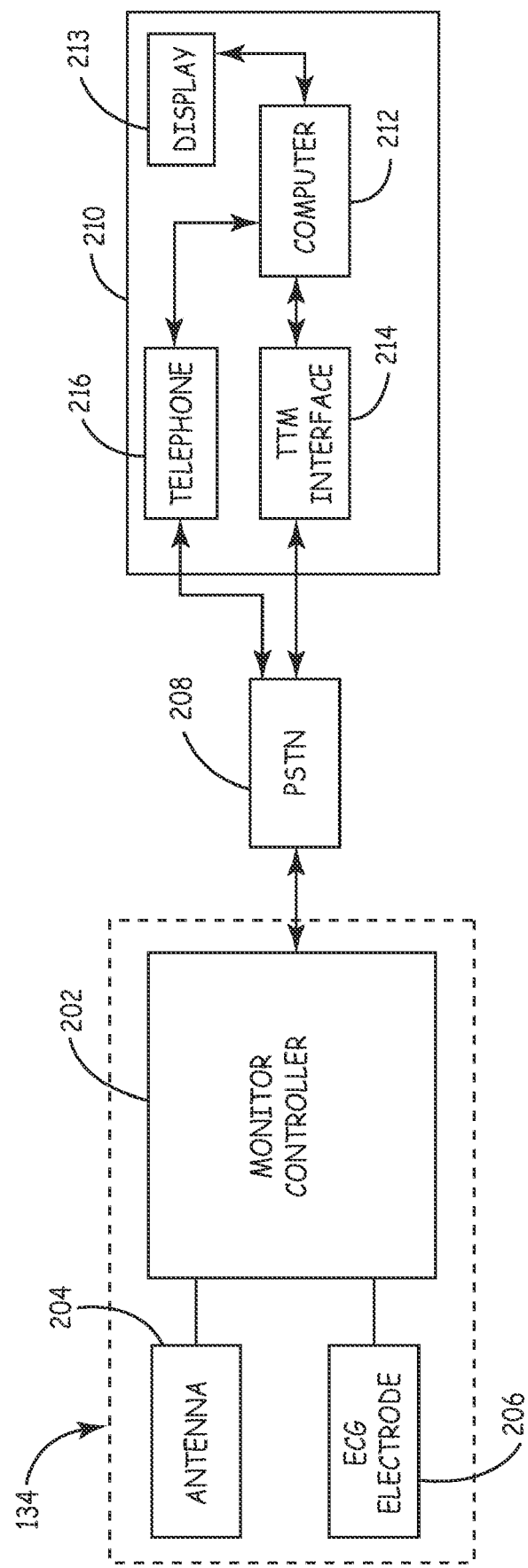
FIG. 2 is a block diagram of a system for interrogating the IMD shown in FIG. 1 to obtain data and for transmitting the obtained data to a remote site.

As FIG. 1 additionally shows, the IPG 100 is capable of both transmitting 126 and receiving 128 data. This may be accomplished in any one of numerous ways, but in the depicted embodiment this is accomplished via telemetry transmission using any one of numerous known modulation schemes. Thus, the IPG 100 includes a small antenna 132 that is used, in conjunction with other circuitry within the IPG housing 102 that is described in more detail below, to transmit 126 data to, and to receive 128 data from, one or more external patient monitors 134. The data that the IPG 100 transmits to, and receives from, the patient monitor 134, will depend, at least in part, on the type and purpose of the patient monitor 134. For example, the patient monitor 134 may be a programming device that a physician or other practitioner uses to program or reprogram the overall operation, or portions thereof, of the IPG 100. Moreover, as will be described in more detail further below, the patient monitor 134, in accordance with a particular preferred embodiment, may be a patient monitoring device that is used to interrogate the IPG 100 and, in response to the interrogation, receive various data from the IPG 100 for subsequent transmission. An exemplary embodiment of this latter type of patient monitor 134 and its interconnection to other external devices is shown in FIG. 2, and will now be described in more detail.

The patient monitoring device 134 includes a monitor controller 202, a monitor antenna 204, and one or more pair of electrocardiogram (ECG) electrodes 206. The monitor controller 202 is connected to the public switched telephone system (PSTN) 208. In response to an input from a user such as, for example, pressing a button or other input device (not shown) on the monitor controller 202, or in response to command signals received via PSTN 208, the monitor controller 202 begins transmitting interrogation signals to the monitor antenna 204. The monitor antenna 204 emits these interrogation signals, which are in turn received by the IPG antenna 132. Again, as will be described in more detail below, in response to the interrogation signals received by the IPG antenna 132, the IPG 100 transmits, among other things, various types of real-time device- and physiologic-related data, via the IPG antenna 132. The real-time data transmitted from the IPG 100 is received by the monitor antenna 204 and is transferred to the monitor controller 202. In turn, the monitor controller 202 transmits, in real-time, the data it receives to a remote monitoring station 210, via the PSTN 208. The ECG electrodes 206 are coupled to an external part of the patient's body, and are used to supply surface ECG signals to the monitor controller 202, which may also be transmitted, in real-time, to the remote monitoring station 210, via the PSTN 208.

Figure 8:
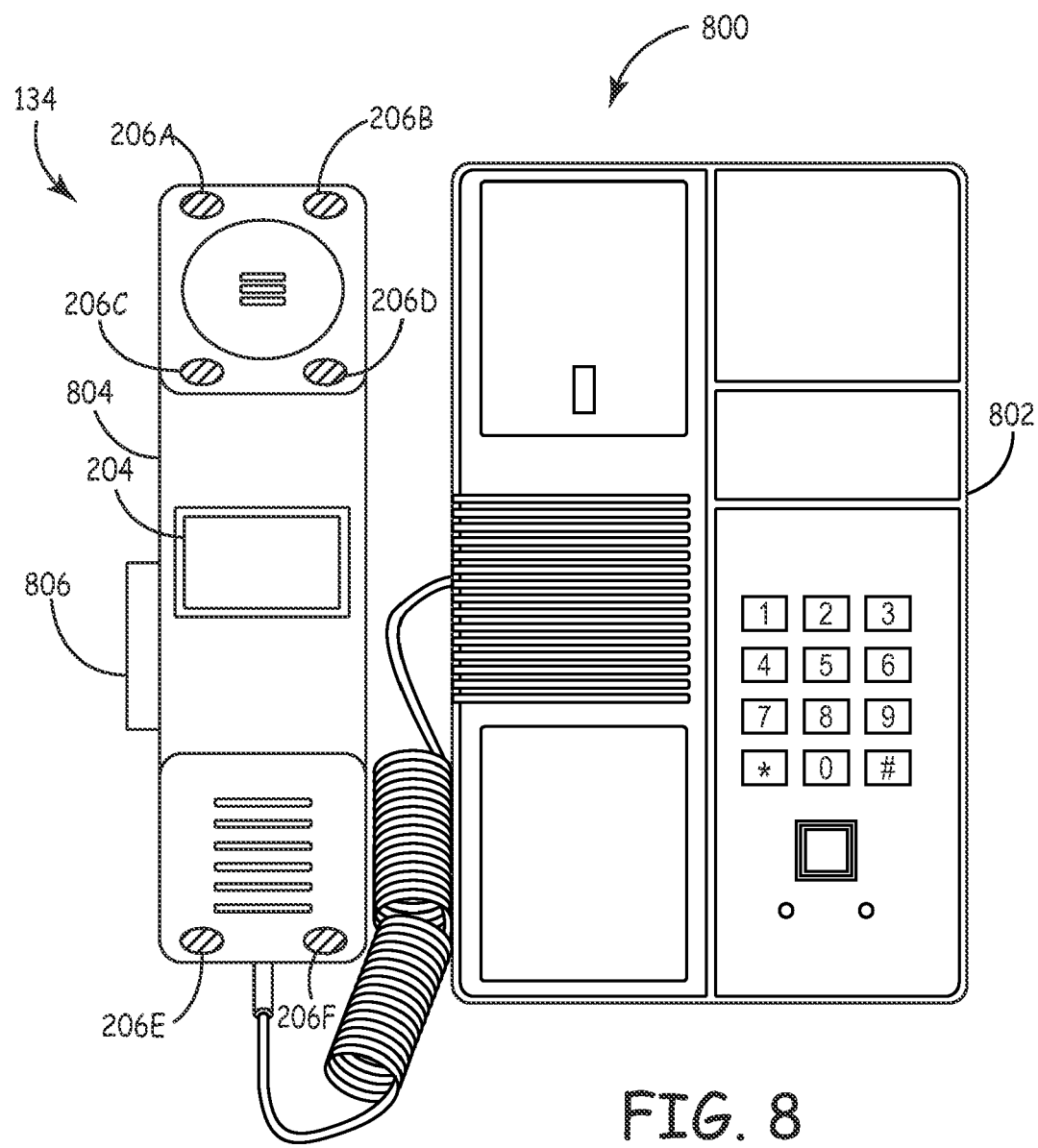
FIGS. 8 and 9 are physical embodiments of a patient monitor that may be used to implement a portion of the system depicted in FIG. 2.
Figure 9:
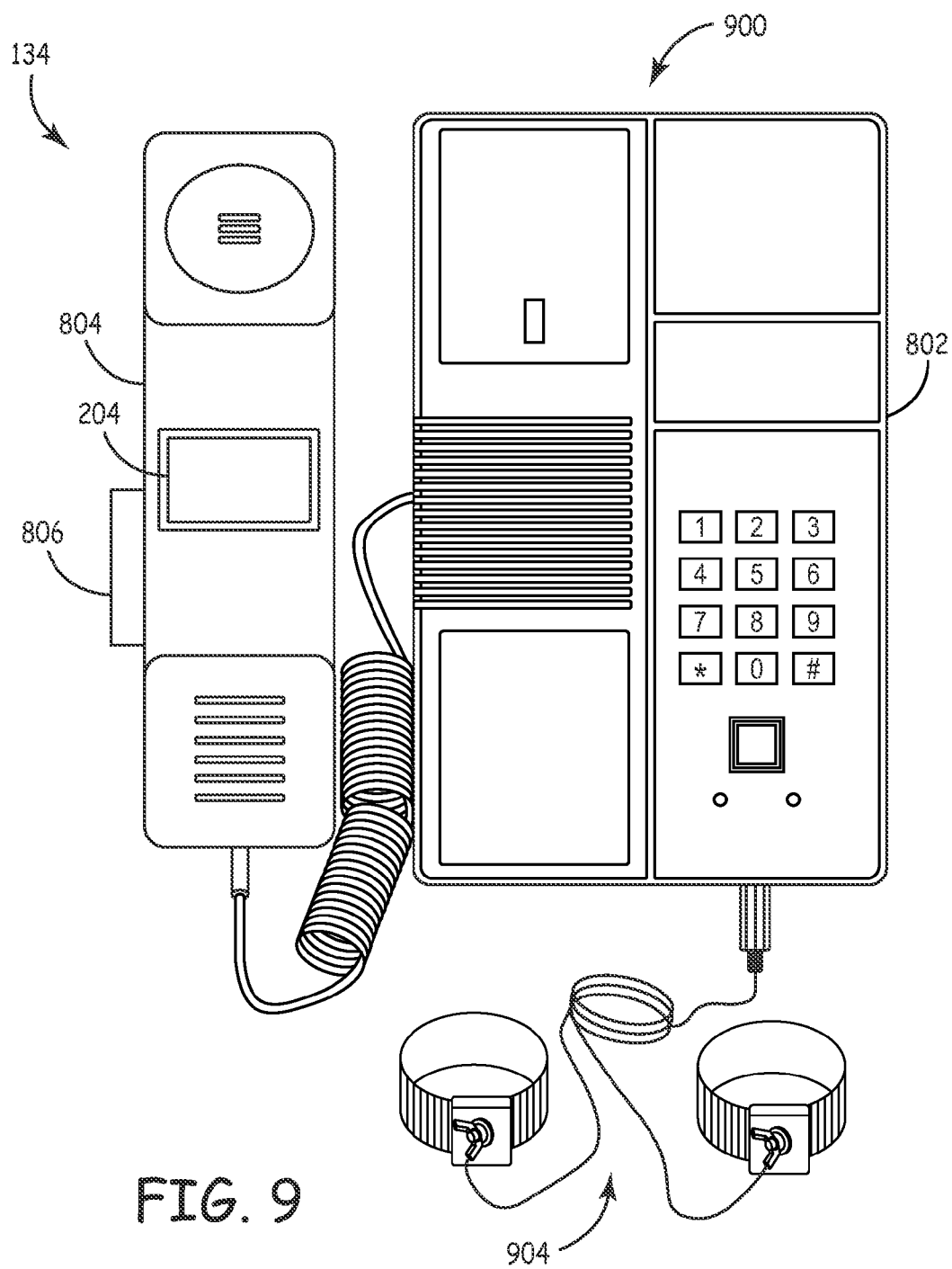

It will be appreciated that the patient monitor 134 could be implemented in any one of numerous forms, such as the physical implementation shown in FIG. 8, in which the patient monitor is implemented as an integral part of a telephone 800, which includes a base 802 and a handset 804. In the depicted implementation, the ECG electrodes 206A-206F, and the monitor antenna 204 are disposed in the handset 804, and the monitor controller 202 is disposed in the base 802. The handset 804 additionally includes an external port 806 that is adapted to receive one or more cables that are electrically coupled to one or more convention ECG electrodes. An alternative physical embodiment is depicted in FIG. 9, in which one or more conventional ECG electrodes 902 are coupled to the base 802.

Returning once again to FIG. 2, it is seen that the remote monitoring station 210 preferably includes a computer 212, a telephone 214, a TTM (transtelephonic modulation) interface 216. The computer 212 may be selectively, or continuously, coupled to the PSTN 208, via the TTM interface 216. The TTM interface 214 receives various signals from the patient monitoring device 134, via the PSTN 208, demodulates various data from the received signals, and supplies the demodulated data to the computer 212. The type of data demodulated from the received signals is described in more detail further below. In any case, the computer 212 includes appropriate hardware and software drivers to display, in real-time, the data transmitted from the patient monitor 134 to the remote monitoring station 210. The telephone 216 is preferably coupled to the PSTN 208 in a conventional manner, and is used by an operator (not illustrated) at the remote monitoring station 210 to communicate with, for example, the patient into whom the IPG 100 is implanted. In particular, the remote operator preferably calls the patient and steps the patient through various preliminary operations, which are discussed further below, in order to transmit various information about the IPG 100 and the patient to the remote monitoring station 210.

Figure 3:
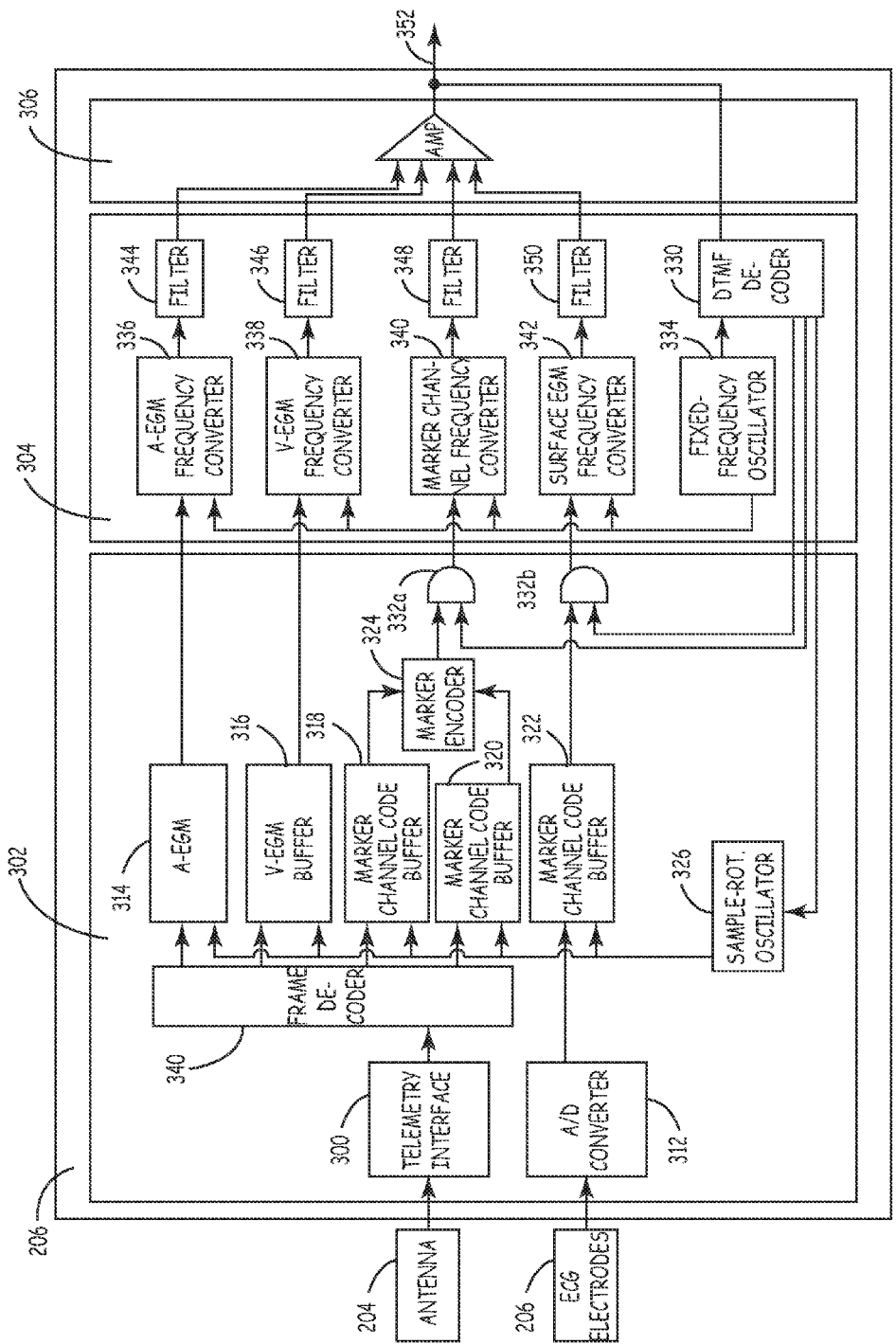
FIG. 3 is a functional block diagram of a monitor controller that may be used to implement the system of FIG. 2.

Turning now to FIG. 3, a detailed description of a particular preferred embodiment of the monitor controller 202 will now be described. As FIG. 3 shows, the monitor controller 202 includes an input circuit 302, a frequency modulation circuit 304, and an amplifier circuit 306. The input circuit 302 is coupled to the monitor antenna 204 and the ECG electrodes 206. Thus, the input circuit 302 receives the RF signals transmitted from the IPG 100 and received by the antenna 204, and the surface ECG signals supplied from the ECG electrodes 206. The input circuit 302 demodulates digital data from the RF signals transmitted from the IPG 100, and converts the analog surface ECG signals into digital format.

In a particular preferred embodiment, the digital data that is demodulated from the RF signal includes EGM data and marker channel data. Preferably, the EGM data includes both atrial EGM (A-EGM) and ventricular EGM (V-EGM) data values. The marker channel data, as is generally known, includes data values representative of both sensed and stimulated physiological events. In particular, the sensed physiological events include atrial and ventricular events that are sensed by the IPG 100. Such events include, for example, atrial and ventricular depolarizations. The stimulated physiological events include both atrial and ventricular stimulus signals that are supplied by the IPG 100. Such events include, for example, atrial and ventricular pacing pulses supplied by the IPG 100 to the atrium and ventricle, respectively.

The RF signal transmitted by the IPG 100, as previously noted, may be modulated using any one of numerous modulation schemes. In the depicted embodiment, the RF signal is modulated with digital data values using, for example, a frequency shift key (FSK) modulation scheme, in which the digital data are encoded into data frames. Thus, in the depicted embodiment, the input circuit 302 is implemented using a telemetry interface 308, a frame decoder 310, an analog-to-digital (A/D) converter circuit 312, a plurality of buffer circuits 314, 316, 318, 320, 322, a marker encoder circuit 324, and a sample-rate oscillator circuit 326. The telemetry interface 308 is coupled to receive the RF signals received by the monitor antenna 204 and is configured to demodulate at least the A-EGM, V-EGM, and marker channel data frames from the RF signal. It is noted that the marker channel data frames include data values representative of the type of physiological event (e.g., sense or pace), and data values representative of the relative time of occurrence of the event. The frame decoder 310 then receives the demodulated data frames from the telemetry interface 308 and extracts the specific data values from the demodulated data frames. The surface ECG signals supplied from the ECG electrodes 206 are analog signals. Thus, the A/D converter circuit 312, which is coupled to the ECG electrodes 206, converts the analog surface ECG signals to surface ECG digital data values.

The digital data values that the frame decoder 310 extracts from the demodulated data frames, and the digital surface ECG data values converted in the A/D converter circuit 312 are supplied to selected ones of the data buffer circuits 314-322. Specifically, the demodulated A-EGM data values are supplied to an A-EGM buffer circuit 314, the V-EGM data values are supplied to a V-EGM buffer circuit 316, the data values representative of the type of physiological event is placed in a marker channel code buffer 318, the data values representative of the relative time of occurrence of the physiological event are placed in a marker channel indicator buffer 320, and the digital surface ECG data values are supplied to a surface ECG buffer circuit 322.

The sample-rate oscillator 326 is coupled to each of the buffer circuits 314-322, and controls the rate at which data is transferred out of each of the buffer circuits 314-322. The sample-rate oscillator 326 is preferably a fixed-frequency oscillator that, when operating, supplies a fixed-frequency command signal to each of the buffer circuits 314-322. This fixed frequency may be any one of numerous values, but in a particular preferred embodiment it is 200 Hz. As FIG. 3 also shows, the sample-rate oscillator 326 is further coupled to a DTMF (dual-tone multi-frequency) decoder circuit 330. As will be described in more detail further below, the sample-rate oscillator 326 may be started and stopped in response to command signals received from the DTMF decoder circuit 330. When the sample-oscillator 326 is started and running, the data buffer circuits 314-322, which are configured to be responsive to the signal from the sample-oscillator circuit 326, transfer the digital data values stored therein to other circuits for additional processing. In particular, the digital data values in the A-EGM buffer circuit 314, the V-EGM buffer circuit 316, and the surface ECG buffer circuit 322 are transferred directly to the frequency modulation circuit 304, while the digital data values in the marker channel code buffer circuit 318, and the marker channel indicator buffer circuit 320 are first transferred to the marker channel encoder circuit 324, which then transfers encoded marker channel digital data to the frequency modulation circuit 304. Before proceeding to a detailed description of the frequency modulation circuit 304, a functional description of the marker channel encoder circuit 324 will first be provided.

Figure 4:
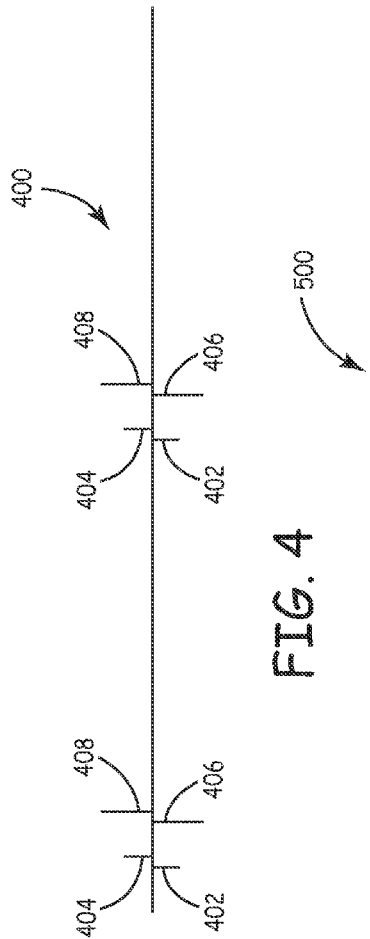
FIG. 4 depicts an exemplary marker channel waveform that may be displayed according to an exemplary embodiment of the present invention.

The marker channel encoder circuit 324 receives the digital data stored in the marker channel code buffer circuit 318, and the digital data stored in the marker channel indicator buffer circuit 320, and supplies encoded marker channel digital data values to the frequency modulation circuit 304. The encoded marker channel digital data values are formatted such that the data values may be suitably processed and displayed at the remote monitoring station 210. The format in which the marker channel digital data values are encoded may be any one of numerous formats that allow each of the sensed and stimulated physiological events to be discriminately displayed. For example, the marker channel encoder circuit 324 formats the encoded marker channel digital values such that the sensed and stimulated physiological events are discriminated by displaying markers of varying pulse amplitude and pulse width. In a particular preferred embodiment, which is shown in FIG. 4, the marker channel encoder circuit 324 formats the encoded marker channel digital data values such that sensed physiological events are displayed with short (e.g., "thin") pulse widths, and stimulated physiological events are displayed with long (e.g., "thick") pulse widths. Moreover, sensed and stimulated atrial events are displayed with lower amplitude pulses as compared to sensed and stimulated ventricular events, which are displayed with higher amplitude pulses. Thus, in the exemplary marker channel display 400 shown in FIG. 4, a sensed atrial event 402 (e.g., an atrial depolarization) is followed by a stimulated atrial event 404 (e.g., an atrial pacing pulse), which is followed by a sensed ventricular event 406 (e.g., a ventricular depolarization), and then a stimulated ventricular event 408 (e.g., a ventricular pacing pulse). Thereafter, at some later point in time, the same sequence is repeated.

Returning once again to FIG. 3, it is seen that the input circuit 302 additionally includes two AND-logic circuits 332a and 332b. The purpose for each of these circuits will be described further below. Before doing so, however, the frequency modulation circuit 304 will be described, and is seen to include a frequency oscillator circuit 334, four frequency generator circuits 336-342, and four filter circuits 344-350.

The frequency oscillator circuit 334 is preferably configured to supply a fixed-frequency drive signal to each of the frequency generator circuits 336-342. The frequency of the drive signal may be any one of numerous values suitable for driving the frequency generator circuits 336-342. In a particular preferred embodiment, the frequency of the drive signal is 16 MHz. It will be appreciated that the frequency oscillator 334 may be any one of numerous known oscillator circuits that provide a fixed-frequency signal. It will additionally be appreciated that the fixed-frequency drive signal may be of any one of numerous types of signals including, for example, sinusoidal, square, and triangular. No matter the particular frequency or shape of the drive signal, this signal is supplied to each of the frequency generator circuits 336-342. The frequency generator circuits 336-342, which will now be described, each supply a carrier signal having a particular central frequency, and that is frequency modulated with the data each frequency generator circuit receives from the input circuit 302.

The frequency generator circuits include an A-EGM frequency generator circuit 336, a V-EGM frequency generator circuit 338, a marker channel frequency generator circuit 340, and an ECG frequency generator circuit 342. The frequency generator circuits 334-340 are each coupled to receive digital data values from the input circuit 302 and, as was mentioned above, the drive signal from the frequency oscillator circuit 334. Specifically, when the sample-rate oscillator 326 supplies a command signal, the A-EGM buffer circuit 314 supplies the A-EGM data value stored therein to the A-EGM frequency generator circuit 336, the V-EGM buffer circuit 316 supplies the V-EGM data value stored therein to the V-EGM frequency generator circuit 338, the marker channel encoder circuit 324 supplies the encoded marker channel digital data value stored therein to the marker channel frequency generator circuit 340, and the ECG buffer circuit 322 supplies the digital surface ECG data value stored therein to the ECG frequency generator circuit 342. The frequency generator circuits 336-342, as was mentioned above, each supply a carrier signal that is frequency modulated with the digital data values it receives. The particular methodology employed within each frequency generator circuit 336-342 to supply the frequency modulated carrier signal will now be described.

In the depicted embodiment, each of the frequency generator circuits 336-342 is implemented as a counter that increments at a frequency based on the drive signal frequency. More specifically, each counter increments at a frequency that is a lower multiple of the drive signal frequency. In particular, each counter includes a frequency offset constant ($k_j$) that divides the drive signal frequency to a lower central frequency value, which is suitable for transmission via the PSTN 208. Additionally, the frequency generator circuits 336-342 each supply an overflow pulse when its counter reaches a predetermined value. Specifically, the overflow pulse supplied by each frequency generator circuit 336-342 correlates to a change in logic level each time the counter reaches the predetermined value. For example, and with reference now to FIG. 5, if the counter supplies a positive-going (or logic "high") overflow pulse 502a on one overflow occurrence, the counter will supply a negative-going (or logic "low") overflow pulse 502b on the subsequent overflow occurrence, and vice-versa. Since the counters each increment at a fixed frequency, the overflow pulses supplied by each frequency generator circuit 336-342 will recur at a frequency that is proportional to the value to which the counter is initialized when it begins incrementing.

Figure 5:
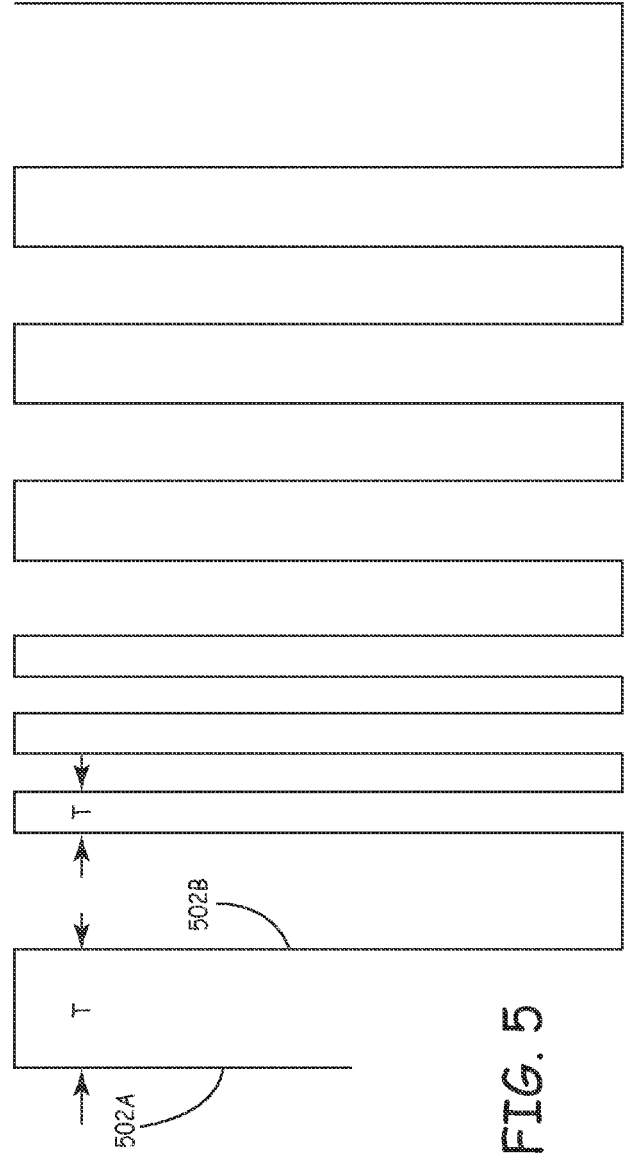
FIG. 5 is an exemplary waveform that illustrates how the monitor controller of FIG. 2 frequency modulates the data the monitor controller obtains from the IMD.

Referring now to FIGS. 3 and 5 together, it will be appreciated that the counter in each frequency generator circuit 336-342 is initialized to a value that is equal, or at least proportional, to the digital data value supplied to it from its corresponding buffer circuit 314-322. Thus, the overflow pulses 502a, 502b generated by each frequency generator circuit 336-342 are supplied at a variable frequency, and represent FM signals modulated with the A-EGM data values, the V-EGM data values, the encoded marker channel digital data values, and the digital surface ECG data values, respectively. It will additionally be appreciated that the time interval (T) between the overflow pulses 502a, 502b is inversely proportional to the value to which the counter in each frequency generator circuit 336-342 is initialized and, as was noted above, is directly proportional to the frequency of the drive signal.

Figure 6:
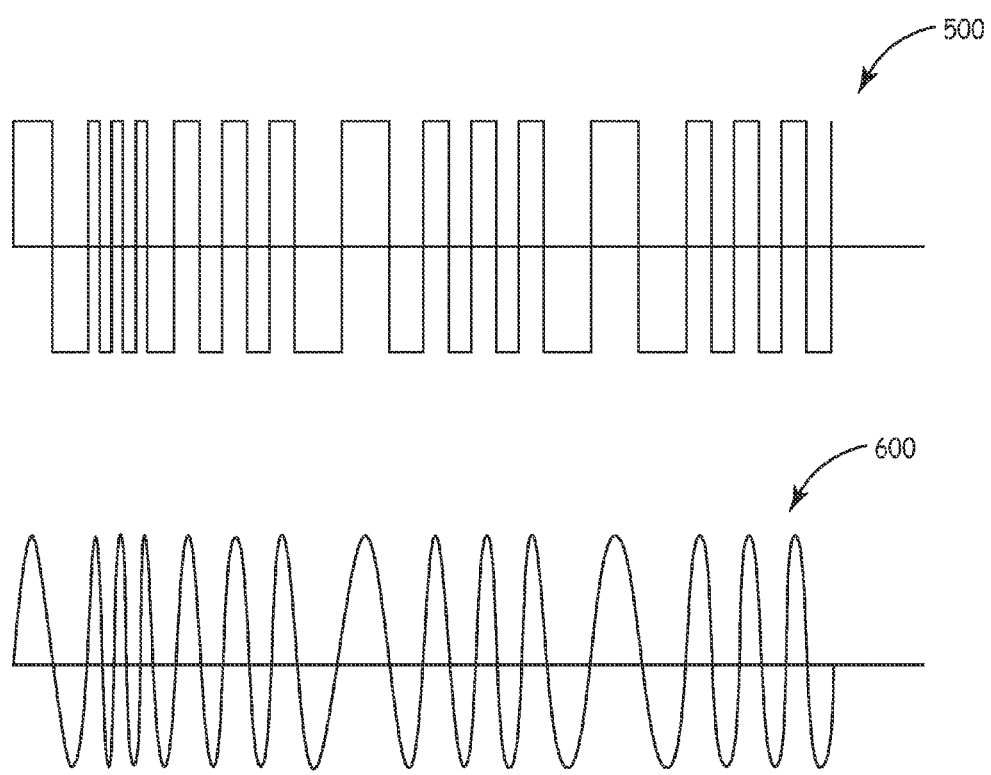
FIG. 6 is a diagram that depicts two waveforms, one is a pre-filtered frequency modulated waveform and the other a post-filtered frequency modulated waveform.

The FM signals 500 supplied from the frequency generator circuits 336-342 are each square waves. Thus, as shown more clearly in FIG. 6, the filter circuits 344-350, which are each coupled to the output of one of the frequency generator circuits 336-342, filter the square wave FM signals 500 and supply a smooth, sinusoidal FM signal 600 to the amplifier circuit 306. It will be appreciated that the filter circuits 344-350 may be implemented as any one of numerous known filter circuit configurations, but are preferably implemented as analog band-pass filter circuits.

The amplifier circuit 306 is coupled to each of the filter circuits 344-350 and is adapted to couple to the PSTN 208 via a conventional telephone line 352. The amplifier circuit 306 combines, in a conventional manner, each of the filtered FM signals supplied from the filter circuits 344-350 into a single, composite FM signal, which is then transmitted to the remote monitoring station 210 via the PSTN 208. It will be appreciated that, in addition to combining the FM signals, the amplifier circuit 306 also provides appropriate impedance matching between the monitor controller 202 and the PSTN 208.

As was previously noted, the monitor controller 202 additionally includes a DTMF decoder circuit 330. The DTMF decoder circuit 330 has an input coupled to the telephone line 352, and at a plurality of outputs. In the depicted embodiment, four of the DTMF decoder circuit outputs are used, one of which is coupled to the sample-rate oscillator 326, a second output is coupled to the frequency oscillator circuit 334, and the a third and fourth outputs are coupled to the AND-logic circuits 332a, 332b. The DTMF decoder circuit 330 receives DTMF signals supplied to the telephone line 352 via the telephone 214 at the remote monitoring station 210. The DTMF decoder circuit 330 is configured to decode the received DTMF signals, and supply appropriate command signals to one of more of the circuits to which the DTMF decoder circuit 330 is coupled. In a particular preferred embodiment, the DTMF decoder circuit 330 is configured to at least supply "start" and "stop" commands to the sample-rate oscillator 326 and the frequency oscillator circuit 334.

The DTMF decoder circuit 330 is further configured to supply appropriate Boolean logic signals to the AND-logic circuits 332a, 332b. These latter commands allow a remote operator to command the monitor controller 202 to transmit either the marker channel data or the surface ECG data simultaneously with the A-EGM data and the V-EGM data. This capability is provided due to the limited bandwidth (e.g., about 3,000 Hz) of conventional telephone lines 352. Because the telephone line bandwidth is limited, it is presently possible to only transmit three combined FM transtelephonic signals simultaneously over the telephone line 352. It will be appreciated that this limitation is only associated with presently available telephone lines and that other transmission media may not be so limited. In such instances, four or more FM signals can be transmitted simultaneously.

Returning now to FIG. 2, it was previously noted that the TTM interface 216 at the remote monitoring station 210 receives and demodulates the data from the FM signal received via the PSTN 208. The demodulation methodology and the hardware used to implement the demodulation methodology may be any one of numerous known methods and hardware configurations. In a particular preferred embodiment, the TTM interface demodulates the received FM signal using the methods and hardware disclosed in U.S. Pat. No. 6,377,843, entitled, "Transtelephonic Monitoring of Multi-Channel ECG Waveforms," which is commonly assigned to the assignee of the present application, and the entirety of which is hereby incorporated by reference. As was previously noted, at least three channels of data are transmitted simultaneously over the telephone line. Thus, the TTM interface 216 is preferably at least a 3-channel device.

Figure 7:
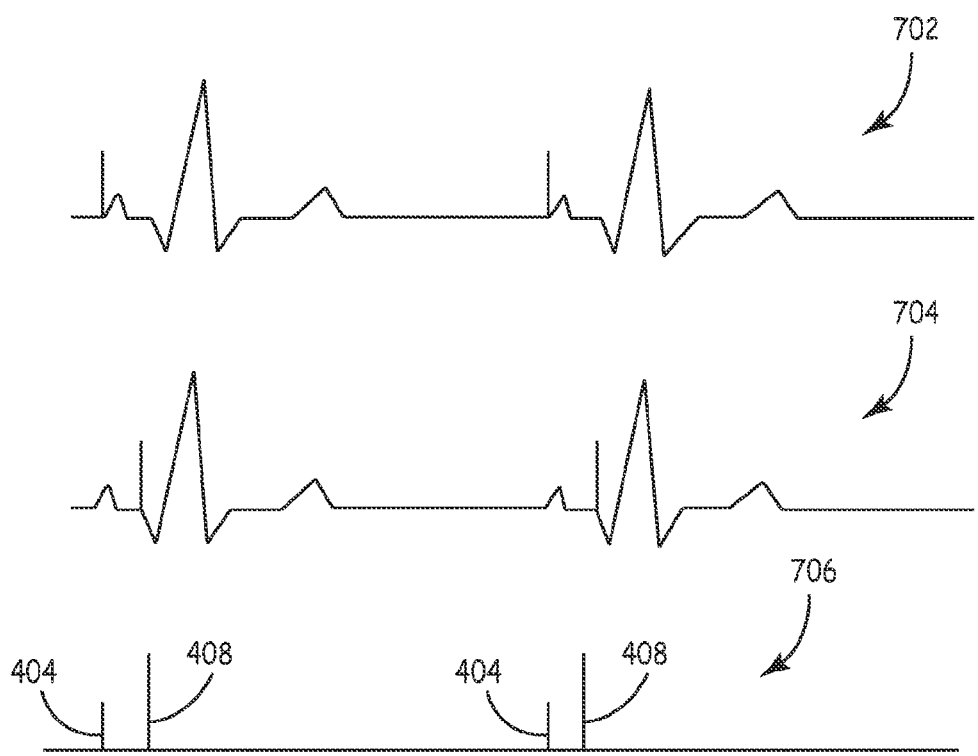
FIG. 7 is a diagram that depicts the simultaneous display of A-EGM data, V-EGM data, and marker channel data in real-time using the system depicted in FIG. 2.

The data that the TTM interface demodulates are sent to the computer 212 for further processing and display on the display device 213. The computer 212 includes appropriate software and display drivers that allow the selected data to be displayed, in real-time, and as analog waveforms, on a display device 213. An exemplary set of waveforms, which include an A-EGM waveform 702, a V-EGM waveform 704, and a marker channel waveform 706, that may be simultaneously displayed in real-time are shown in FIG. 7. As was noted above, when an operator desires to simultaneously display a surface ECG waveform simultaneously with the A-EGM and V-EGM waveforms 702, 704, the operator can depress an appropriate button, or combination of buttons, on the telephone 214. This sends an appropriate DTMF signal to the DTMF decoder circuit 330 in the main monitor controller 202, which in turn commands the monitor controller 202 to transmit the surface ECG data, rather than the marker channel data, with the EGM data. As was additionally noted above, the operator can also provide appropriate DTMF signals to the DTMF decoder circuit 330 to start and stop the sample-rate oscillator 326 and/or fixed-frequency oscillator 334, as desired, to thereby start and stop transmission of the data.

The system and method described herein provides for real-time collection transmission, and simultaneous display at a remote monitoring site, of implant-related data. It will be appreciated that the above-described embodiment is not limited to transmission of 2-channel EGM data. Indeed, it could be used to transmit 3-channel EGM data.

While an exemplary embodiment(s) has been presented in the foregoing detailed description of the invention, it should be appreciated that a vast number of variations exist. It should also be appreciated that these exemplary embodiments are only examples, and are not intended to limit the scope, applicability, or configuration of the invention in any way. Rather, the foregoing detailed description will provide those skilled in the art with a convenient road map for implementing a preferred embodiment of the invention. It being understood that various changes may be made in the function and arrangement of elements described in an exemplary preferred embodiment without departing from the spirit and scope of the invention as set forth in the appended claims.

The invention claimed is:

1. An implant monitor for monitoring an implantable medical device (IMD), the monitor comprising:

an RF receiver adapted to receive an RF signal transmitted from the IMD, the RF signal modulated with at least first and second electrogram (EGM) data, the RF receiver configured to demodulate the first and second EGM data from the received RF signal, the RF receiver comprising a telemetry interface adapted to receive the modulated RF signals transmitted from the IMD and configured to demodulate one or more data frames therefrom, each data frame including at least the first and second EGM data;

a frame decoder circuit coupled to receive the demodulated data frames and configured to extract the first and second EGM data therefrom, respectively;

a sample-rate oscillator circuit operable to supply data sample command signals;

first and second EGM data buffer circuits in operable communication with the frame decoder, each EGM data buffer coupled to receive the data sample command signals and operable, in response thereto, to selectively retrieve the first and second EGM data, respectively, from the frame decoder;

a frequency modulation circuit coupled to receive the demodulated first and second EGM data and a substantially fixed-frequency signal and configured to frequency modulate the fixed-frequency signal based on the demodulated first and second EGM data and supply first and second frequency modulated EGM data signals; and an amplifier circuit coupled to receive the first and second frequency modulated EGM data signals and configured to supply a composite frequency modulated signal.

2. The monitor of claim 1, wherein:

the RF signal is further modulated with data representative of sensed physiological activity;

the RF receiver is further configured to demodulate the sensed physiological activity data from the received RF signal; and the monitor further comprises a marker encoder coupled to receive the demodulated physiological activity data and configured to supply an encoded marker signal that includes data representative of physiological activity type and relative time of occurrence thereof.

3. The monitor circuit of claim 2, wherein the frequency modulation circuit is further coupled to receive the encoded marker signal and is further configured to frequency modulate the fixed frequency signal based on the encoded marker signal and supply a frequency modulated marker signal.

4. The monitor of claim 1, wherein:

the RF signal is further encoded with data representative of real-time physiological stimulus signals generated by the IMD;

the RF receiver is further configured to decode the real-time physiological stimulus signal data from the received RF signal; and the monitor further comprises:

a marker encoder coupled to receive the decoded real-time physiological stimulus signal data and configured to supply encoded marker signal that includes data representative of physiological stimulus type and relative time of occurrence thereof.

5. The monitor of claim 4, wherein the frequency modulation circuit is further coupled to receive the encoded marker signal and is further configured to modulate the fixed-frequency signal based on the encoded marker signal and supply a frequency modulated marker signal.

6. The monitor of claim 1, wherein:

the RF signal is further encoded with data representative of (i) sensed physiological activity and (ii) physiological stimulus signals generated by the IMD;

the RF receiver is further configured to decode (i) the sensed physiological activity data and (ii) the physiological stimulus signal data from the received RF signal; and the monitor further comprises:

a marker encoder coupled to receive the decoded physiological activity data and the decoded physiological stimulus signal data and configured to supply an encoded marker signal that includes data representative of physiological activity type, physiological stimulus type, and relative time of occurrence thereof, respectively.

7. The monitor of claim 6, wherein the frequency modulation circuit is further coupled to receive the encoded marker signal and is further configured to modulate the fixed-frequency signal based on the encoded marker signal and supply a frequency modulated marker signal.

8. The monitor of claim 7, further comprising:

one or more pair of electrocardiogram (ECG) electrodes coupled the RF receiver and configured to supply analog surface ECG signals, wherein:

the RF receiver is further adapted to receive analog electrocardiogram (ECG) signals and supply digital ECG data values representative thereof, and the frequency modulation circuit is further coupled to receive the digital ECG data values and the substantially fixed-frequency signal and is further configured to frequency modulate the fixed-frequency signal based on the digital ECG data values and supply frequency modulated ECG data to the amplifier circuit.

9. The monitor of claim 8, further comprising:

a dual-tone multi-frequency (DTMF) controller coupled to the RF receiver, the DTMF controller adapted to receive DTMF signals from a telephone line and operable, in response thereto, to selectively supply operator command signals, wherein the RF receiver is further operable, in response to the operator command signals, to selectively supply the digital ECG data values to the frequency modulation circuit.

10. The monitor of claim 1, wherein the frequency modulation circuit comprises:

fixed-frequency oscillator circuit operable to supply the substantially fixed-frequency signal;

first and second EGM frequency converters coupled to receive the first and second EGM data from the first and second data buffers, respectively, and further coupled to receive the fixed-frequency signal, the first and second EGM frequency converters configured, in response thereto, to supply the first and second frequency modulated EGM data signals, respectively.

11. The monitor of claim 10, wherein the frequency modulation circuit further comprises:

first and second filter circuits coupled to receive the first and second frequency modulated EGM data signals from the first and second EGM frequency converters, respectively, each filter circuit operable to supply a substantially sinusoidal frequency modulated EGM data signal.

12. The monitor of claim 10, further comprising:

a dual-tone multi-frequency (DTMF) controller coupled to the sample-rate oscillator and fixed-frequency oscillator, the DTMF controller adapted to receive DTMF signals from a telephone line and operable, in response thereto, to selectively supply operator command signals to the sample-rate oscillator and the fixed-frequency oscillator, wherein the sample-rate oscillator and fixed-frequency oscillator are each further operable, in response to the operator command signals, to selectively start and stop in response to the operator command signals.

13. The monitor of claim 1, wherein the amplifier circuit is adapted to couple to a telephone line, to thereby supply the composite frequency modulated signal thereto.

* * * * *